US009721749B2

(12) United States Patent
Hirose et al.

(10) Patent No.: US 9,721,749 B2
(45) Date of Patent: Aug. 1, 2017

(54) X-RAY GENERATOR AND FLUORESCENT X-RAY ANALYZER

(71) Applicant: HITACHI HIGH-TECH SCIENCE CORPORATION, Tokyo (JP)

(72) Inventors: Ryusuke Hirose, Tokyo (JP); Haruo Takahashi, Tokyo (JP)

(73) Assignee: HITACHI HIGH-TECH SCIENCE CORPORATION, Tokyo (JP)

( * ) Notice: Subject to any disclaimer, the term of this patent is extended or adjusted under 35 U.S.C. 154(b) by 92 days.

(21) Appl. No.: 14/837,745

(22) Filed: Aug. 27, 2015

(65) Prior Publication Data

US 2016/0118215 A1     Apr. 28, 2016

(30) Foreign Application Priority Data

Oct. 27, 2014 (JP) .................................. 2014-217924

(51) Int. Cl.
*G01N 23/223* (2006.01)
*H01J 35/06* (2006.01)
(Continued)

(52) U.S. Cl.
CPC ............ *H01J 35/16* (2013.01); *G01N 23/223* (2013.01); *H01J 35/06* (2013.01); *H01J 35/08* (2013.01); *H05G 1/02* (2013.01)

(58) Field of Classification Search
CPC ................ A61B 6/4405; A61B 6/4488; G01N 2223/204; G01N 2223/419;
(Continued)

(56) References Cited

U.S. PATENT DOCUMENTS

| 3,329,816 A | * | 7/1967 | Grundhauser | ........... H05G 1/02 174/21 JC |
| 4,166,231 A | * | 8/1979 | Braun | ..................... H01J 35/16 378/125 |

(Continued)

FOREIGN PATENT DOCUMENTS

| JP | 58111000 | 7/1983 |
| JP | 6251647 | 3/1987 |

(Continued)

OTHER PUBLICATIONS

European Search Report issued in the corresponding European Patent Application No. 15183160.9, dated Feb. 29, 2016, 8 pages.

*Primary Examiner* — David J Makiya
*Assistant Examiner* — Soorena Kefayati
(74) *Attorney, Agent, or Firm* — Hamre, Schumann, Mueller & Larson, P.C.

(57) ABSTRACT

The present invention provides an X-ray generator including an X-ray tube 2 radiating primary X-rays X1 to a specimen S, a housing 3 accommodating the X-ray tube 2, an X-ray radiation area controller 4 limiting the radiation area of the primary X-rays X1 from the X-ray tube 2 to the specimen S, and a device holder 5 holding the X-ray radiation area controller 4 with respect to the housing 3. The X-ray tube includes a case 6, an electron ray source 7 generating electron rays, and a target unit 8 having a base fixed to the case and receiving electron rays through a protruding free end. The device holder has a fixed-base 5a fixed to the housing, directly under the base of the target unit, and a supporting extension 5b extending from the fixed-base in the protrusion direction of the target unit and supporting the X-ray radiation area controller.

4 Claims, 5 Drawing Sheets (51) Int. Cl.
*H01J 35/08* (2006.01)
*H05G 1/02* (2006.01)
*H01J 35/16* (2006.01)

(58) Field of Classification Search
CPC ..... G01N 2223/612; G01N 2223/1291; G01N 23/223; H01J 35/12; H01J 35/16; H05G 1/02

See application file for complete search history.

(56) References Cited

U.S. PATENT DOCUMENTS

| | | | |
|---|---|---|---|
| 4,217,517 A | 8/1980 | Delair et al. | |
| 6,661,876 B2 * | 12/2003 | Turner | G01N 23/223 313/553 |
| 6,888,923 B2 * | 5/2005 | Dahan | F16C 27/04 378/123 |
| 7,065,174 B2 * | 6/2006 | Sipila | G01N 23/223 378/44 |
| 7,949,092 B2 * | 5/2011 | Brons | G01N 23/223 378/44 |
| 7,963,696 B2 | 6/2011 | Bailey et al. | |
| 9,305,739 B2 * | 4/2016 | Legall | H01J 35/101 |
| 2007/0140420 A1 | 6/2007 | Radley et al. | |

FOREIGN PATENT DOCUMENTS

| | | |
|---|---|---|
| JP | 2007323898 | 12/2007 |
| JP | 2011-071120 | 4/2011 |

\* cited by examiner

X-RAY GENERATOR AND FLUORESCENT X-RAY ANALYZER

CROSS REFERENCE TO RELATED APPLICATION(S)

This application claims the benefit of Japanese Patent Application No. JP 2014-217924, filed on Oct. 27, 2014, which is hereby incorporated by reference in its entirety into this application.

BACKGROUND OF THE INVENTION

1. Technical Field

The present invention relates to an X-ray generator suitable for a fluorescent X-ray analyzer that can detect harmful substances and is used for screening a product or measuring thickness of a film such as a plated layer, and a fluorescent X-ray analyzer having the same.

2. Description of the Related Art

Fluorescent X-ray analysis is a process wherein X-rays are radiated to a specimen from an X-ray tube, fluorescent X-rays coming out of the specimen are detected using an X-ray detector, and components of the specimen is qualitatively analyzed or concentration or film thickness is quantitatively analyzed from the intensity relationship of the X-rays. Fluorescent X-ray analysis makes it possible to quickly and nondestructively analyze a specimen, so it is used in various fields including process/quality management. In recent years, with the development of precision and sensitivity, fluorescent X-ray analysis can measure small amount of a substance and is expected as an analysis technique to detect harmful substances, particularly in materials or composite electronic parts.

In general, a fluorescent X-ray analyzer that analyzes a range of tens to hundreds of micrometers by narrowing primary X-rays to be radiated to a specimen into a narrow beam is equipped with a device for limiting an X-ray radiation area and an X-ray tube that is an X-ray source (hereafter, referred to an X-ray radiation area controller or a condensing element). For example, there is a fluorescent X-ray analyzer equipped with a poly-capillary that can reduce a radiation area on a specimen by condensing X-rays from an X-ray tube. The poly-capillary is a device that is composed of a bundle of hollow glass tubes (capillaries) having an inner diameter of about 10 μmm and condenses X-rays by totally reflecting incident X-rays from the inner side such that the exits of the capillaries focus on one point.

It is required to make sure that the X-ray generation position in the X-ray tube and the X-ray radiation area controller are precisely aligned. However, the temperature around an X-ray tube changes in a predetermined range in many cases due to various factors such as the installation environment of the apparatus, heat generation in the case of the tube, and a temperature change in the case due to opening/closing of a door. Due to this change, the amount of thermal deformation of the anode of the X-ray tube is usually changed, and accordingly, the X-ray generation position is changed.

That is, the temperature of an X-ray tube is not uniform throughout it due to the output, the environment temperature, and the temperature in the case of the apparatus and the X-ray tube thermally deforms due to the temperature change, so the mechanical position of the X-ray generator changes. Accordingly, in an apparatus for radiating X-rays to a specific small area and analyzing fluorescent X-rays coming from the area, a mechanical change of an X-ray generation position causes misalignment of a device for radiating X-rays to the specific small area, so the X-ray radiation position or the intensity of the X-rays is changed.

For example, when a poly-capillary is attached and fixed to an X-ray source, condensing efficiency (intensity of output from the poly-capillary) depends on the attachment position of the poly-capillary, and maximum output intensity is achieved when the poly-capillary is disposed directly under the X-ray generation position relative to the target of the X-ray tube. In this case, when the relative position between the X-ray source and the poly-capillary changes due to a mechanical factor or heat (temperature drift), the output intensity is reduced. In particular, the output intensity is sensitive in the horizontal direction perpendicular to the central axis of the poly-capillary. For example, the output intensity is reduced by 5% point when it moves 10 μm in the horizontal direction.

These changes have conventionally been handled by suppressing a change in atmospheric temperature through interior air-conditioning or by performing corrective measurement for frequently correcting an effect of temperature change, but they are insufficient.

In relation to these problems, a system for moving a target of an X-ray tube by heating/cooling the target in accordance with a change in surrounding temperature and for correcting position alignment due to a temperature change have been proposed in Patent Document 1.

DOCUMENTS OF RELATED ART

Patent Document

Japanese Patent Application Publication No. 2011-71120

SUMMARY OF THE INVENTION

The above related art has the following problems.

That is, in the technology described in Patent Document 1, there is a need for a plurality of devices such as a temperature sensor and a temperature actuator for controlling the temperature of a target and complicated and high-precise temperature control is required. Accordingly, this problem increases the price of the system.

Accordingly, the present invention has been made keeping in mind the above problems occurring in the prior art, and an object of the present invention is to provide an X-ray generator that can suppress misalignment of a device for limiting an X-ray generation position and an X-ray radiation area with a relatively simple configuration, and a fluorescent X-ray analyzer including the X-ray generator.

The present invention employs the following configuration to solve the problems. In order to accomplish the above object, the present invention provides an X-ray generator that includes: an X-ray tube radiating primary X-rays to a specimen; a housing accommodating the X-ray tube; an X-ray radiation area controller limiting a radiation area of the primary X-rays from the X-ray tube to the specimen; and a device holder holding the X-ray radiation area controller with respect to the housing, in which the X-ray tube includes a vacuumized case, an electron ray source disposed as a cathode in the case and generating electron rays, and a target unit disposed as an anode facing the electron ray source in the case, with a base fixed to the case, and receiving electron rays through a protruding free end, the device holder has a fixed-base fixed to the housing, directly under the base of the target unit, and a supporting extension extending from the fixed-base in a protrusion direction of the target unit and supporting the X-ray radiation area controller.

In the X-ray generator, since the device holder has a fixed-base fixed to the housing, directly under the base of the target unit, and a supporting extension extending from the fixed-base in a protrusion direction of the target unit and supporting the X-ray radiation area controller, it is possible to suppress a change in relative position between the free end of the target unit and the X-ray radiation area controller even if there is thermal expansion. That is, the X-ray radiation area controller is held by the supporting extension extending in the same direction in the shape of a cantilever, similar to the target unit, and the supporting extension thermally extends in the same direction as the thermal expansion of the target unit. Accordingly, even if the X-ray generation position is moved from the free end of the target unit by thermal expansion, the supporting extension also thermally expands, so the X-ray radiation area controller held by the supporting extension moves the same displacement in the same direction. Therefore, even if there is thermal expansion due to a change in surrounding temperature, the relative position between the free end of the target unit and the X-ray radiation area controller is not easily changed, so a change in output intensity can be suppressed.

In the X-ray generator, a thermal expansion rate in an extension direction of the supporting extension may be the same as a thermal expansion rate in the protrusion direction of the target unit.

That is, in the X-ray generator, since the thermal expansion rate in an extension direction of the supporting extension may be the same as the thermal expansion rate in the protrusion direction of the target unit, even if the target unit thermally expands in the protrusion direction due to a change in surrounding temperature, the supporting extension changes in length in the extension direction with the same thermal expansion rate, so the relative position between the free end of the target unit and the X-ray radiation area controller is not changed.

In the X-ray generator, the supporting extension may be made of the same material as the target unit, and a distance from the portion fixed to the housing to a central axis of the X-ray radiation area controller may be the same as a distance from the base to an X-ray generation position at the free end of the target unit.

That is, in the X-ray generator, since the supporting extension is made of the same material as the target unit, and the distance from the portion fixed to the housing to a central axis of the X-ray radiation area controller is the same as the distance from the base to an X-ray generation position at the free end of the target unit, the supporting extension thermally expands in the same amount as the thermal expansion of the target unit due to a change in surrounding temperature, so the relative position between the X-ray generation position of the target unit and the X-ray radiation area controller is not changed.

In the X-ray generator, the device holder may have a guide that guides the supporting extension such that the supporting extension can thermally expand in the extension direction.

That is, in the X-ray generator, since the device holder has a guide that guides the supporting extension such that the supporting extension can thermally expand in the extension direction, the supporting extension is guided by the guide and the supporting extension is prevented from bending in directions except for the extension direction, so it is possible to prevent vertical misalignment except for the extension direction.

The present invention provides a fluorescent X-ray analyzer that includes: the X-ray generator and a detector detecting fluorescent X-rays coming out of the specimen receiving the primary X-rays.

That is, since the fluorescent X-ray analyzer includes the X-ray generator, a change in output intensity is small and high-precision fluorescent X-ray analysis is possible.

According to the present invention, the following effects are accomplished.

That is, according to the X-ray generator and the fluorescent X-ray generating apparatus, since the device holder has a fixed-base fixed to the housing, directly under the base of the target unit, and a supporting extension extending from the fixed-base in a protruding direction of the target unit and supporting the X-ray radiation area controller, it is possible to suppress a change in relative position between the free end of the target unit and the X-ray radiation area controller even if there is thermal expansion. Accordingly, it is possible to suppress a change in output intensity.

Therefore, it is possible to suppress misalignment between the X-ray generator and the X-ray radiation area controller, using a relatively simple configuration, so it is possible to suppress a change in output intensity.

BRIEF DESCRIPTION OF THE DRAWINGS

The above and other specimens, features and advantages of the present invention will be more clearly understood from the following detailed description taken in conjunction with the accompanying drawings, in which.

DESCRIPTION OF THE PREFERRED EMBODIMENTS

The present invention will be described in detail below with reference to the accompanying drawings. Repeated descriptions and descriptions of known functions and configurations which have been deemed to make the gist of the present invention unnecessarily obscure will be omitted below. The embodiments of the present invention are intended to fully describe the present invention to a person having ordinary knowledge in the art to which the present invention pertains. Accordingly, the shapes, sizes, etc. of components in the drawings may be exaggerated to make the description clearer.

Figure 1:
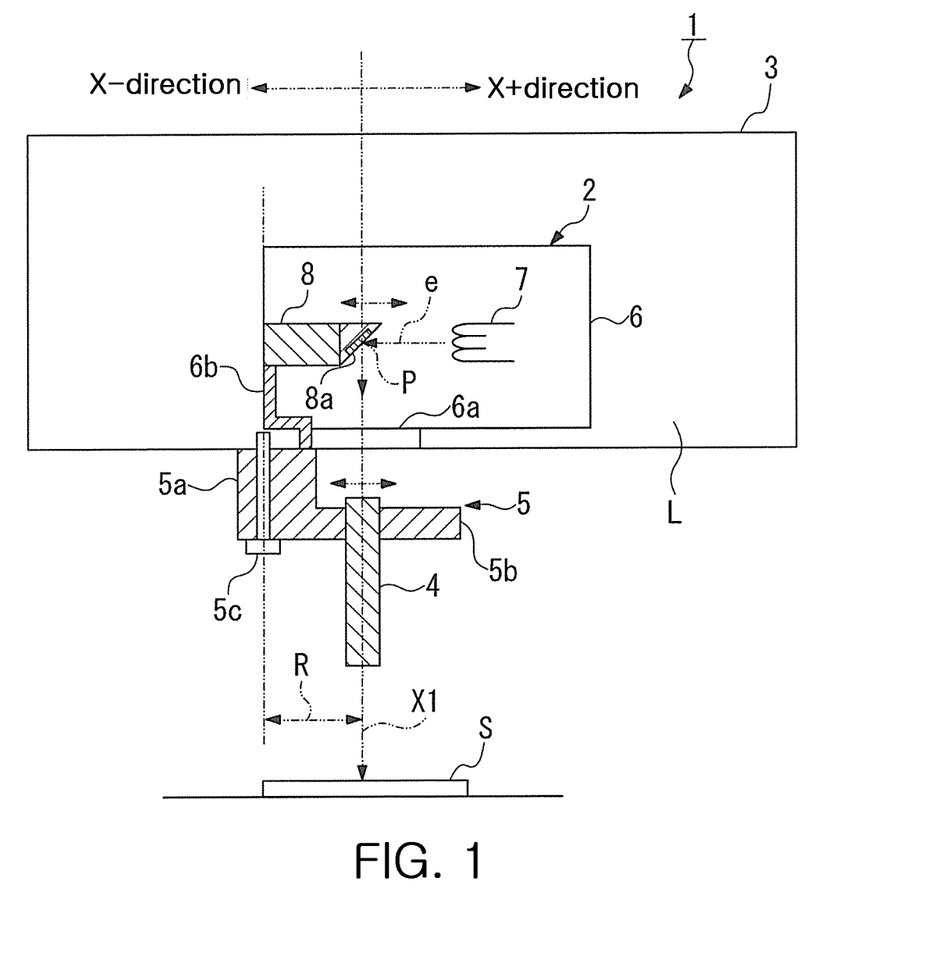
FIG. 1 is a cross-sectional view showing an X-ray generator in a first embodiment of an X-ray generator and a fluorescent X-ray analyzer according to the present invention.
Figure 2:
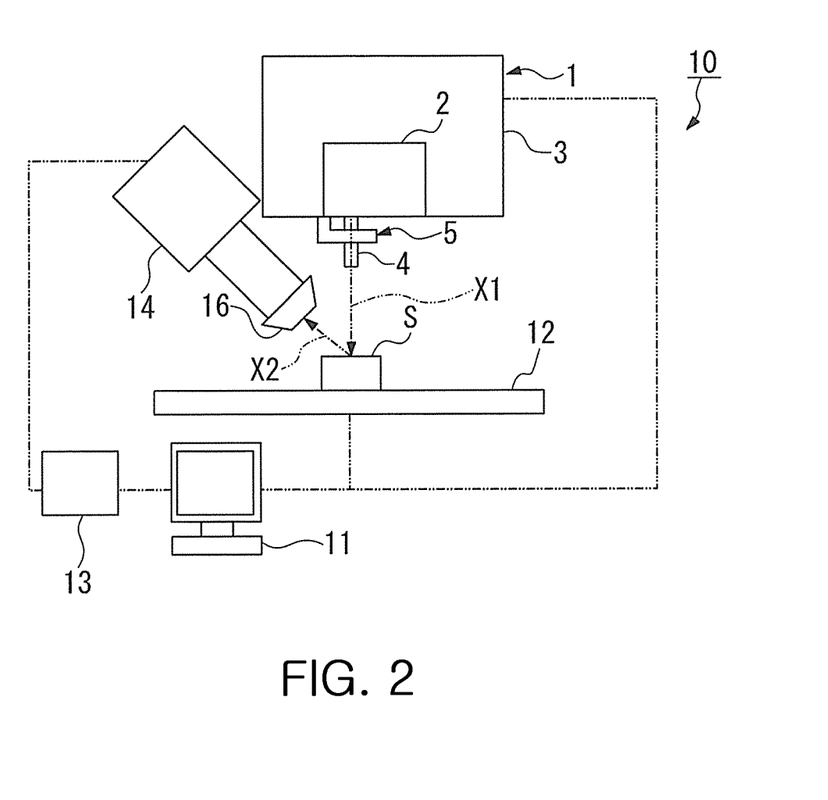
FIG. 2 is a view showing the entire configuration of the fluorescent X-ray analyzer in the first embodiment.

A first embodiment of an X-ray generator and a fluorescent X-ray analyzer according to the present invention is described hereafter with reference to FIGS. 1 and 2.

An X-ray generator 1 of the present embodiment, as shown in FIG. 1, includes an X-ray tube 2 radiating primary X-rays X1 to a specimen S, a housing 3 accommodating the X-ray tube 2, an X-ray radiation area controller 4 limiting the radiation area of the primary X-rays X1 from the X-ray tube 2 to the specimen S, and a device holder 5 holding the X-ray radiation area controller 4 with respect to the housing 3.

The X-ray tube 2 includes a case 6 with a vacuum inside, an electron ray source 7 disposed as a cathode in the case 6 and generating electron rays 'e', and a target unit 8 disposed as an anode facing the electron ray source 7 in the case 6, with the base fixed to the case 6, and receiving electron rays 'e' through a protruding free end 8a.

The device holder 5 has a fixed-base 5a fixed to the housing 3, directly under the base of the target unit 8 and a supporting extension 5b extending from the fixed-base 5a in the protrusion direction of the target unit 8 and supporting the X-ray radiation area controller 4. That is, the device holder 5 has an L-shaped cross-section. The fixed-base 5a is fixed to the bottom of the housing 3 by a fixing bolt 5c.

The supporting extension 5b, similar to the target unit 8, has the structure of a cantilever with a first end that is fixed as the base and a second end that is a free end.

The thermal expansion rate of the supporting extension 5b in the extension direction is set to be the same as the thermal expansion rate of the target unit 8 in the protrusion direction.

The supporting extension 5b is made of the same material as the target unit 8 and the distance R from the portion fixed to the housing 3 to the central axis of the X-ray radiation area controller 4 is set to be the same as the distance from the base to an X-ray generation position P at the free end 8a of the target unit 8 In the present embodiment, the target unit 8, fixed-base 5a, and supporting extension 5b are made of copper (Cu).

The X-ray tube 2 can radiate primary X-rays X1, electron rays (thermal electrons) 'e' generated from a filament (cathode) that is the electron ray source 7 therein is accelerated by a voltage applied between the electron ray source 7 and the target unit (anode) 8, and an X-ray, which is generated by hitting against copper (Cu), tungsten (W), molybdenum (Mo), and chromium (Cr) of the target unit 8, is radiated as the primary X-rays X1 through a window 6a, for example, made of beryllium. Further, as described above, in the present embodiment, the target unit 8 is made of copper (Cu).

The X-ray tube 2 is put in high-pressure insulating oil L and disposed in the housing 3.

The X-ray radiation area controller 4 may be, for example, a collimator, a mono-capillary, or a poly-capillary. In particular, in the present embodiment, a poly-capillary is used as the X-ray radiation area controller 4. The X-ray radiation area controller 4 has a base disposed directly under the X-ray generation position P at the free end 8a of the target unit 8 to receive primary X-rays X from the X-ray tube 2 and a free end that faces a specimen bed 12 and radiates the condensed primary X-rays X1. The device holder 5 holds the base of the X-ray radiation area controller 4 directly under the window 6a and holds the X-ray radiation area controller 4 with the X-ray generation position P aligned with the central axis of the X-ray radiation area controller 4 (central axis of the poly-capillary), using the supporting extension 5b.

The X-ray radiation area controller 4 that is a condensing element is a poly-capillary, but may be a converging crystal. Alternatively, the X-ray radiation area controller 4 may be, instead of a condensing element, a collimator that limits an X-ray radiation area by partially blocking primary X-rays X1.

Next, the fluorescent X-ray analyzer 10 of the present embodiment includes the X-ray generator 1, a detector 14 that detects fluorescent X-rays X2 coming out of a specimen S receiving primary X-rays X1, an analyzer 13 that is connected to the detector 14 and analyzes a signal from the detector 14, and a controller 11 that is connected to the X-ray generator 1, the detector 14, and the analyzer 13.

The detector 14 includes a semiconductor detection element (for example, a silicon element that is a pin diode) (not shown), and outputs a voltage signal including information of the energy and incident timing of an X-ray photon, using a pre-amplifier connected to the rear side, by generating a charge corresponding to one X-ray photon, when one X-ray photon is received.

The specimen S is placed on the specimen bed 12, which is an XY stage, for analysis.

The controller 11 is a computer connected to the specimen bed 12 and includes a CPU controlling the X-ray tube 2, detector 14, and specimen bed 12.

The analyzer 13 is a pulse height analyzer (multi-channel pulse height analyzer) that obtains the height of a voltage pulse from the signal and generates an energy spectrum.

When the fluorescent X-ray analyzing unit 10 performs analysis, the primary X-rays X1 radiated from the target unit 8 of the X-ray tube 2 is narrowed to a desired radiation diameter by the X-ray radiation area controller 4 that is a poly-capillary and then travels to the specimen S. The detector 14 receives fluorescent X-rays X2 coming out of the specimen S and the fluorescent X-rays are analyzed.

In this analysis, when the target unit 8 increases in temperature and thermally expands in the protrusion direction (the X+ direction in FIG. 1), the X-ray generation position P at the free end 8a of the target unit 8 moves in the expansion direction. However, the heat of the target unit 8 is transmitted also to the device holder 5 through the case 6 and the housing 3, the temperature of the device holder 5 increases to the level of the temperature of the target unit 8. Accordingly, the supporting extension 5b thermally expands in the extension direction (X+ direction in FIG. 1) in the same way, so the X-ray radiation area controller 4 held by the supporting extension 5b also moves in the extension direction of the supporting extension 5b equal to the displacement of the X-ray generation position P. Accordingly, even if the temperature of the target unit 8 changes, misalignment between the X-ray generation position P and the X-ray radiation area controller 4 is suppressed.

As shown in FIG. 1, a thermal conductive passage 6b made of copper and connecting the portion where the target unit 8 is fixed to the case 6 to the portion where the fixed-base 5a is in contact with the housing 3 may be further provided. Accordingly, heat is more quickly transmitted from the target unit 8 to the fixed-base 5a through the thermal conductive passage 6b, so the temperature difference between the target unit 8 and the device holder 5 can be quickly removed, and accordingly, the effect of suppressing misalignment between the X-ray generation position P and the X-ray radiation area controller 4 increases.

As described above, in the X-ray generator 1 and the fluorescent X-ray analyzer 10 according to the present embodiment, since the device holder 5 has the base fixed to the housing 3 directly under the base of the target unit 8 and the supporting extension 5b extending in the protrusion direction of the target unit 8 from the fixed-base 5a and supporting the X-ray radiation area controller 4, it is possible to suppress a relative position change between the free end 8a of the target unit 8 and the X-ray radiation area controller 4 even if there is thermal expansion.

That is, since the X-ray radiation area controller 4 is held by the supporting extension 5b extending in a cantilever type in the same direction as the target unit 8, the supporting extension 5b thermally expands in the thermal expansion direction of the target unit 8. Accordingly, even if the X-ray generation position P at the free end 8a of the target unit 8 changes, the supporting extension 5b also thermally expands, so the X-ray radiation area controller 4 held by the supporting extension 5b also moves the same displacement in the same direction. Therefore, even if there is thermal expansion due to a change in surrounding temperature, the relative position between the free end 8a of the target unit 8 and the X-ray radiation area controller 4 is not easily changed, so a change in output intensity can be suppressed.

Further, since the thermal expansion rate of the supporting extension 5b in the expansion direction is the same as the thermal expansion rate of the target unit 8 in the protrusion direction, even if the target unit 8 thermally expands in the protrusion direction due to a change in surround temperature, the supporting extension 5b changes in length in the extension direction with the same thermal expansion rate, such that the relative position between the free end 8a of the target unit 8 and the X-ray radiation area controller 4 is not changed.

In particular, since the supporting extension 5b is made of the same material as the target unit 8 and the distance from the portion fixed to the housing 3 to the central axis of the X-ray radiation area controller 4 is the same as the distance from the base to the X-ray generation position P at the free end 8a of the target unit 8, the amount of thermal expansion of the target unit 8 due to a change in surrounding temperature is the same as that of the supporting extension 5b and the relative position between the X-ray generation position P of the target unit 8 and the X-ray radiation area controller 4 is not changed.

Therefore, since the fluorescent X-ray analyzer 10 according to the present embodiment includes the X-ray generation source 21, a change in output intensity is small and high-precision fluorescent X-ray analysis is possible.

Next, a second embodiment and a third embodiment of an X-ray generation source and fluorescent X-rays analyzer according to the present invention are described with reference to FIGS. 3, 4A, 4B, and 4C. In the following description of embodiments, the same components described in the previous embodiment are given the same reference numerals and not described.

Figure 3:
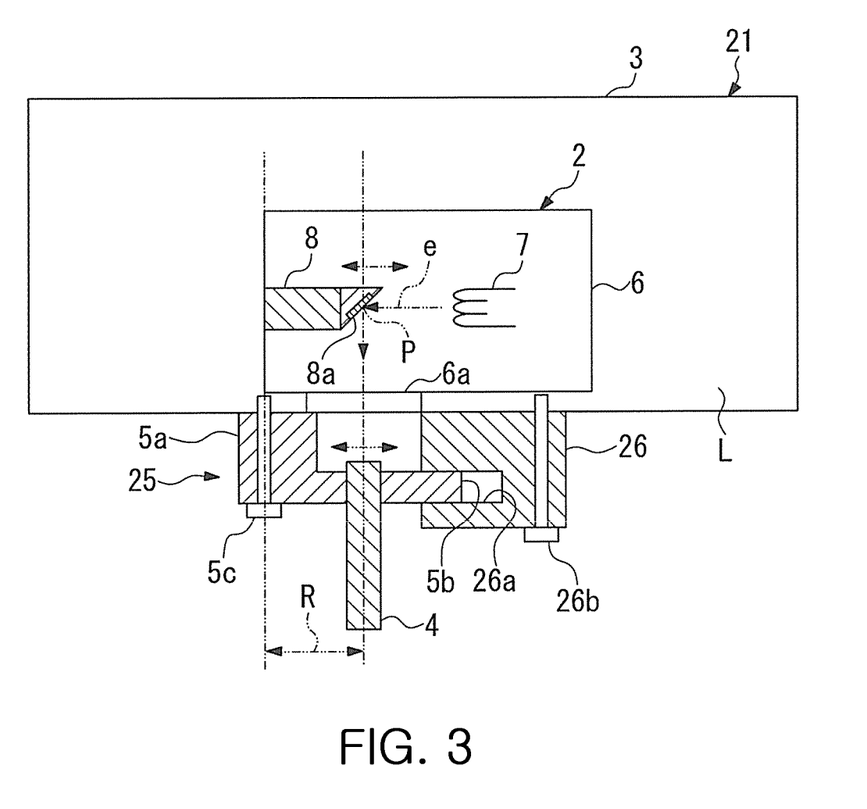
FIG. 3 is a cross-sectional view showing an X-ray generator in a second embodiment of an X-ray generator and a fluorescent X-ray analyzer according to the present invention.

The difference between the second embodiment and the first embodiment is that the supporting extension 5b of the device holder 5 is supported only at one end (base) by the fixed-base 5a in the first embodiment, while in an X-ray generation source 21 of the second embodiment, a device holder 25 has a guide 26 for guiding the supporting extension 5b such that the supporting extension 5b can thermally extend in the extension direction, as shown in FIG. 3. That is, in the second embodiment, the guide 26, which is disposed around the free end of the supporting extension 5b and has a groove 26a having a U-shaped cross-section to support the top and bottom of the supporting extension 5b, is fixed to the bottom of the housing 3 by a bolt 26b.

The groove 26a is formed deep in the extension direction of the supporting extension 5b and the supporting extension 5b is inserted in the groove 26a. Accordingly, the supporting extension 5b can extend/contract in the extension direction with the top and bottom retained.

The guide is made of a low-thermal expansion material such as steel, Fe—Ni 36% alloy or cast iron having a graphite structure in an austenitic iron matrix.

Accordingly, in the second embodiment, since there is provided the guide 26 that guides the supporting extension 5b of the device holder 5 capable of thermally expanding in the extension direction, the supporting extension 5b is guided by the guide 26 and the supporting extension 5b is prevented from bending up/down in thermal expansion, so it is possible to prevent vertical misalignment.

Figure 4A:
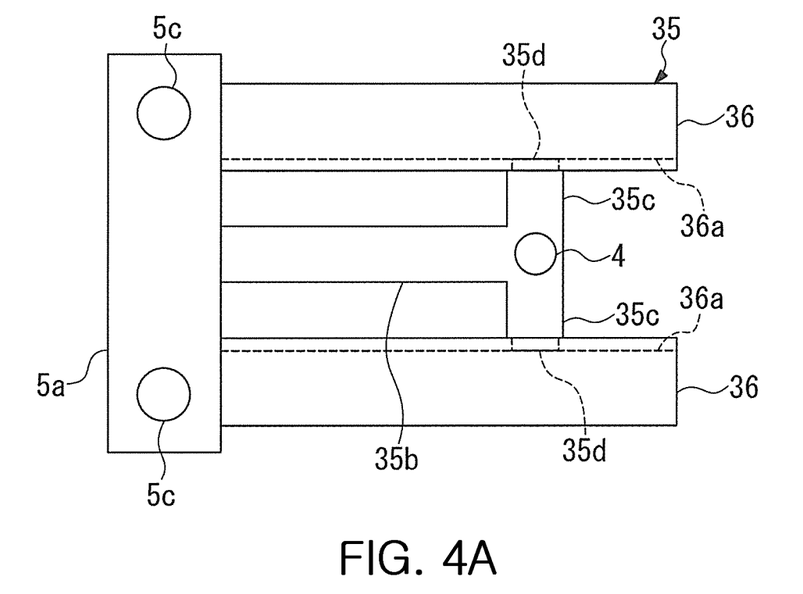
FIGS. 4A to 4C are a bottom view, a right side view B, and a front view, respectively, showing a device holder in a third embodiment of an X-ray generator and a fluorescent X-ray analyzer according to the present invention.
Figure 4B:
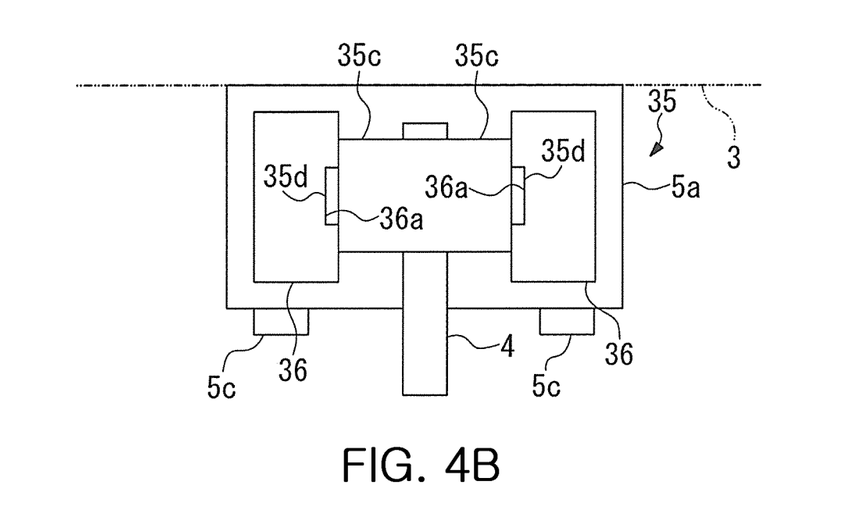
Figure 4C:
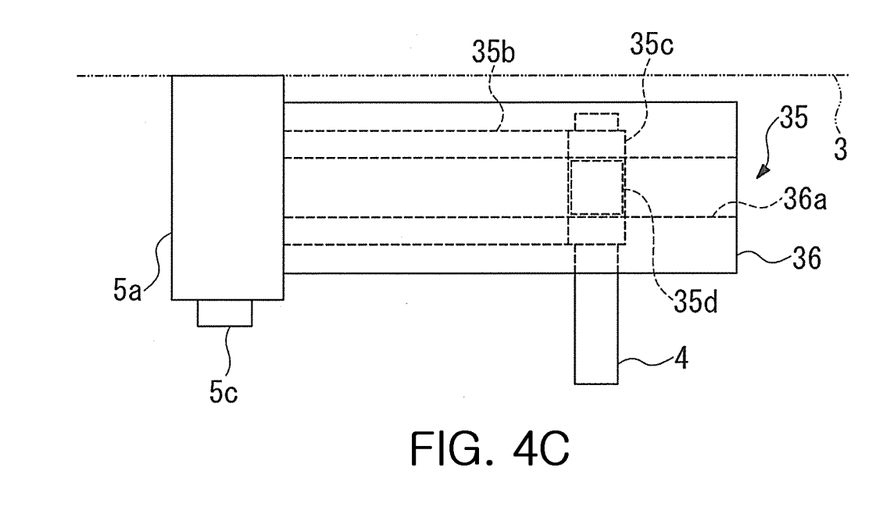

Next, the difference between the third embodiment and the second embodiment is that the guide 26 supports the top and bottom of the supporting extension 5b in the second embodiment, whereas in the third embodiment, the X-ray generator 1 has a guide 36 having a pair of support rods 36 that can support both sides of the supporting extension 5b, as shown in FIGS. 4A to 4C. That is, in the third embodiment, the guide 36 has a pair of support rods 36 having bases fixed to the fixed-base 5a and a slit 36a in which free end 35c of a supporting extension 35b is fitted to be movable in the extension direction of the support rods 36 is formed on the inner sides of the support rods 36.

The supporting extension 35b has an extension rod 35b extending in the protrusion direction of the target unit 8 and a pair of free ends 35c protruding to both sides from the free end of the extension rod 35b. That is, the supporting extension 35b has a T-shape, when seen from above.

The ends of the free ends 35c are fitted in the slits 36a, so the free end 35c can move in the extension direction of the extension rod 35b. Further, the X-ray radiation area controller 4 that is a poly-capillary is attached between the pair of free ends 35c.

As described above, in the third embodiment, the supporting extension 35b is supported not only vertically, but laterally by the guide 26, so the supporting extension 35b is prevented from bending not only vertically, but laterally in thermal expansion. Accordingly, it is possible to prevent not only vertical misalignment, but lateral misalignment (horizontal, perpendicular to the extension direction).

Further, the scope of the present invention is not limited to the embodiments and may be modified in various ways without departing from the spirit of the present invention.

For example, the present invention has been applied to an energy division type of fluorescent X-ray analyzer that measures the energy and intensity of X-rays using a pulse height analyzer in the embodiments, but it may be applied to a wavelength analysis type of fluorescent X-ray analyzing unit that divides fluorescent X-rays using a spectrum crystal and measures the wavelength and intensity of the X-ray.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

As described above, optimal embodiments of the present invention have been disclosed in the drawings and the specification. Although specific terms have been used in the present specification, these are merely intended to describe the present invention and are not intended to limit the meanings thereof or the scope of the present invention described in the accompanying claims. Therefore, those skilled in the art will appreciate that various modifications and other equivalent embodiments are possible from the embodiments. Therefore, the technical scope of the present invention should be defined by the technical spirit of the claims.

What is claimed is:

1. An X-ray generator, comprising:
an X-ray tube radiating primary X-rays to a specimen;
a housing accommodating the X-ray tube;

an X-ray radiation area controller limiting a radiation area of the primary X-rays from the X-ray tube to the specimen; and a device holder holding the X-ray radiation area controller with respect to the housing, wherein the X-ray tube includes a vacuumized case, an electron ray source disposed as a cathode in the case and generating electron rays, and a target unit disposed as an anode facing the electron ray source in the case, with a base fixed to the case, and receiving electron rays through a protruding free end, the device holder has a fixed-base fixed to the housing, directly under the base of the target unit, and a supporting extension extending from the fixed-base in a protrusion direction of the target unit and supporting the X-ray radiation area controller, a thermal expansion rate in an extension direction of the supporting extension from the fixed-base in the same direction as the protrusion direction of the target unit is the same as a thermal expansion rate in the protrusion direction of the target unit, and a distance from a portion of the supporting extension fixed to the housing to a central axis of the X-ray radiation area controller is the same as a distance from the base to an X-ray generation position at the free end of the target unit.

2. The X-ray generator of claim 1, wherein the supporting extension is made the same material as the target unit.

3. The X-ray generator of claim 1, wherein the device holder has a guide that guides the supporting extension such that the supporting extension can thermally expand in the extension direction.

4. A fluorescent X-ray analyzer comprising the X-ray generator of claim 1 and a detector detecting fluorescent X-rays coming out of the specimen receiving the primary X-rays.

* * * * *